US012758245B2

(12) United States Patent
Spector

(10) Patent No.: US 12,758,245 B2
(45) Date of Patent: Oct. 13, 2026

(54) TRANSCATHETER DEVICE FOR SCORING CALCIFICATIONS AND FOR CUTTING VALVE TISSUE

(71) Applicant: Pi-Cardia Ltd., Rehovot (IL)

(72) Inventor: Benzion Spector, Be'er Yaakov (IL)

(73) Assignee: PI-CARDIA LTD., Rehovot (IL)

( * ) Notice: Subject to any disclaimer, the term of this patent is extended or adjusted under 35 U.S.C. 154(b) by 237 days.

(21) Appl. No.: 18/681,092

(22) PCT Filed: Aug. 9, 2022

(86) PCT No.: PCT/IB2022/057418
§ 371 (c)(1),
(2) Date: Feb. 5, 2024

(87) PCT Pub. No.: WO2023/017417
PCT Pub. Date: Feb. 16, 2023

(65) Prior Publication Data

US 2024/0268850 A1 Aug. 15, 2024

Related U.S. Application Data

(60) Provisional application No. 63/231,826, filed on Aug. 11, 2021.

(51) Int. Cl.
*A61B 17/32* (2006.01)
*A61B 17/00* (2006.01)
*A61B 17/22* (2006.01)

(52) U.S. Cl.
CPC ........ *A61B 17/32* (2013.01); *A61B 17/00234* (2013.01); *A61B 17/22* (2013.01);
(Continued)

(58) Field of Classification Search
CPC ... A61B 17/32; A61B 17/00234; A61B 17/22; A61B 2017/00243; A61B 2017/00292;
(Continued)

(56) References Cited

U.S. PATENT DOCUMENTS

2005/0250988 A1* 11/2005 Ewers .................. A61B 1/0014 600/102
2006/0064113 A1* 3/2006 Nakao ............ A61B 17/320016 606/113
(Continued)

FOREIGN PATENT DOCUMENTS

JP 2008-534069 8/2008
JP 2010-525867 7/2010
(Continued)

OTHER PUBLICATIONS

PCT Search Report and Written Opinion PCT/IB2022/057418, Nov. 9, 2022.

*Primary Examiner* — Katrina M Stransky
(74) *Attorney, Agent, or Firm* — PEARL COHEN LLP

(57) ABSTRACT

A transcatheter device (10) includes a first jaw member (12), a second jaw member (14) and a linkage mechanism (16) coupled to the first and second jaw members (12, 14) for changing a distance between the first and second jaw members (12, 14). At least one of the first and second jaw members (12, 14) includes scoring structure (20) capable of scoring calcifications or tissue or any other anatomical structure, with a direction of a scoring force along a jaw closing axis (25) that extends between surfaces (22, 24) of the first and second jaw members (12, 14), respectively, which face each other. The first jaw member (12) has a cutting element (18) arranged to cut in a cutting direction (27) transverse to the jaw closing axis (25).

12 Claims, 10 Drawing Sheets

(52) U.S. Cl.
CPC ............... *A61B 2017/00243* (2013.01); *A61B 2017/00292* (2013.01); *A61B 2017/00477* (2013.01); *A61B 2017/22098* (2013.01); *A61B 2017/32006* (2013.01)

(58) Field of Classification Search
CPC ........... A61B 2017/00477; A61B 2017/22098; A61B 2017/32006; A61B 2017/22097; A61B 2017/2944
See application file for complete search history.

(56) References Cited

U.S. PATENT DOCUMENTS

| | | | | |
|---|---|---|---|---|
| 2007/0078459 | A1* | 4/2007 | Johnson | A61B 17/320016 606/51 |
| 2010/0036370 | A1* | 2/2010 | Mirel | A61B 18/1445 606/45 |
| 2011/0306972 | A1* | 12/2011 | Widenhouse | A61B 18/1445 606/41 |
| 2013/0289602 | A1 | 10/2013 | Kobayashi | |
| 2014/0228871 | A1 | 8/2014 | Cohen | |
| 2015/0164533 | A1* | 6/2015 | Felder | A61B 18/1445 606/169 |
| 2016/0278847 | A1* | 9/2016 | Batchelor | A61B 18/1445 |
| 2017/0119459 | A1 | 5/2017 | Schechter et al. | |
| 2018/0280084 | A1* | 10/2018 | Hancock | A61B 18/1815 |
| 2020/0146690 | A1* | 5/2020 | Rothstein | A61B 18/1445 |
| 2021/0007768 | A1 | 1/2021 | Lin et al. | |

FOREIGN PATENT DOCUMENTS

| | | |
|---|---|---|
| JP | 2012-501736 | 1/2012 |
| JP | 2016-083298 | 5/2016 |
| JP | 2020-503090 | 1/2020 |
| JP | 2020-512038 | 4/2020 |
| WO | WO2020/234763 | 11/2020 |

* cited by examiner

TRANSCATHETER DEVICE FOR SCORING CALCIFICATIONS AND FOR CUTTING VALVE TISSUE

CROSS-REFERENCE TO RELATED APPLICATIONS

This application is a National Phase Application of PCT International Application No. PCT/IB2022/057418, International Filing Date Aug. 9, 2022, claiming priority to U.S. Provisional Patent Application No. 63/231,826, filed Aug. 11, 2021, which is hereby incorporated herein by reference in its entirety.

FIELD OF THE INVENTION

The present invention generally relates to devices and methods for transcatheter cutting of heart valve calcification and heart valve tissue.

BACKGROUND OF THE INVENTION

PCT Patent Application PCT/IB2020/054729 describes a transcatheter valve laceration device and method. The invention is a method and device, which can be used to perform BASILICA (Bioprosthetic or native Aortic Scallop Intentional Laceration to prevent Iatrogenic Coronary Artery obstruction). The device is a cutting device with attention to preventing damage to neighboring tissues. The device can be implemented in other cardiologic procedures, such as tricuspidization of a bicuspid valve (turning a bicuspid valve into a tricuspid valve by cutting or splitting one of the bicuspid leaflets into two leaflets) or tricuspidization of a quadricuspid valve (lacerating one of the leaflets to turn the valve into a tricuspid valve), thereby preparing the patient for safe transcatheter aortic valve replacement (TAVR), or for other procedures that involve cutting cardiac tissue.

SUMMARY OF THE INVENTION

The present invention seeks to provide a transcatheter device which can be used to score calcifications in heart valves and can also be used as a laceration device to cut or slice (the terms being used interchangeably) heart tissue. Accordingly, the device of the invention can be used to perform BASILICA and other cutting procedures and can be used simultaneously to score calcifications at the cutting site. The term "scoring" refers to any kind of reduction in size or any modification in shape or form, such as but not limited to, scoring, cutting, fracturing, pulverizing, breaking, grinding, chopping and the like. The device can be used in treatments of the aortic valve, mitral valve, and other cardiac tissues. The device may be introduced using a transfemoral, transaortic, transsubclavian, transapical, transseptal or any other percutaneous approach. For example, in a transseptal access, the device may be installed in a reversed orientation over the device delivery system.

In accordance with a non-limiting embodiment of the present invention, the transcatheter valve laceration device includes a cutting element mounted on a guiding structure. The cutting element is expandable and contractible with respect to the guiding structure. The guiding structure is deliverable to a heart valve and the cutting element is expanded and moved (in a direction which may be different than the expansion direction) towards the valve leaflets to cut them. A support structure may be provided on the opposite side of the valve leaflets to act as an "anvil" against the cutting force of the cutting element and to protect tissues, which should not be cut, from the cutting element.

BRIEF DESCRIPTION OF THE DRAWINGS

The present invention will be understood and appreciated more fully from the following detailed description, taken in conjunction with the drawings in which:

FIGS. 11-25 are simplified pictorial illustrations of components of the transcatheter device and their assembly with each other, wherein:

FIG. 11 illustrates a cutter mover which will be coupled to the cutting element at a distal end thereof;

FIG. 12 illustrates the cutter mover coupled to the cutting element;

FIG. 13 illustrates the cutter mover coupled to the cutting element from a different viewing angle, showing the inner portion of the cutting element;

FIG. 14 illustrates a distal end of the first jaw member;

FIG. 15 illustrates a side-view of the first jaw member;

FIG. 16 illustrates the assembly of the cutter mover and the cutting element assembled in the first jaw member;

FIG. 17 illustrates a pivot member which will be coupled to the first jaw member;

FIG. 18 illustrates the pivot member coupled to the first jaw member;

FIG. 19 illustrates a linkage mechanism which will be coupled to the first and second jaw members for changing the distance between the first and second jaw members, wherein in the illustrated non-limiting embodiment the linkage mechanism is a foldable hinged parallelogram mechanism;

FIG. 20 illustrates the linkage mechanism coupled to the pivot member of the first jaw member;

FIG. 21 illustrates the linkage mechanism deployed outwards from the first jaw member;

FIG. 22 illustrates the linkage mechanism deployed outwards from the first jaw member as seen from a different view;

FIG. 23 illustrates an actuator interface member configured to move one or more stabilizing arms of the transcatheter device;

FIG. 24 illustrates the one or more stabilizing arms coupled to the actuator interface member;

FIG. 25 illustrates the one or more stabilizing arms and the actuator interface member coupled to the first jaw member of the transcatheter device.

DETAILED DESCRIPTION OF EMBODIMENTS

Figure 1:
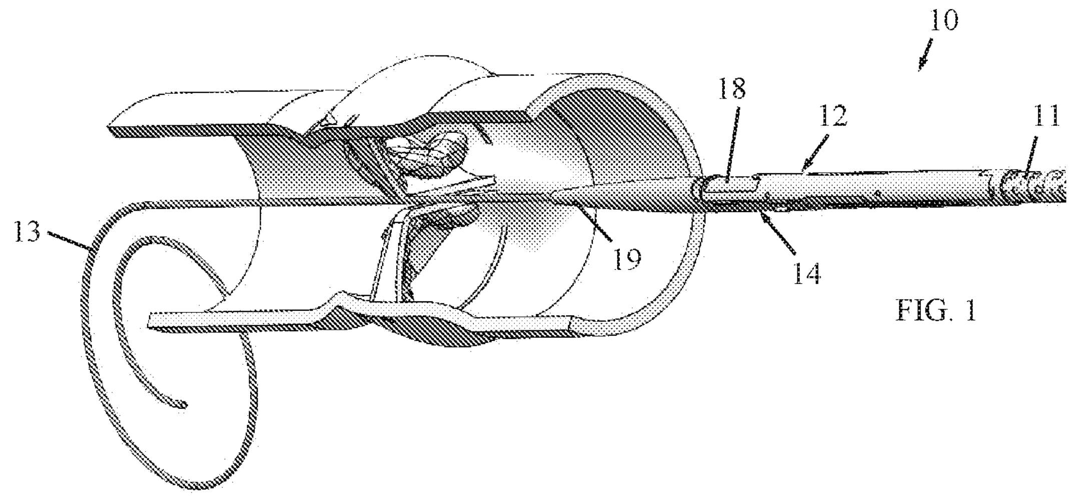
FIG. 1 is a simplified pictorial illustration of a transcatheter device, constructed and operative in accordance with a non-limiting embodiment of the invention, in a stowed (contracted) orientation and being deployed over a guidewire to the surgical site.

Reference is now made to FIGS. 1-6, which illustrate a transcatheter device 10, constructed and operative in accordance with a non-limiting embodiment of the invention.

First, a general description of the main sub-assemblies of the device is given and then later more specific descriptions of the parts are given.

There are three main sub-assemblies of the device 10 (all three seen in FIG. 3): a first jaw member 12, a second jaw member 14 and a linkage mechanism 16 coupled to the first and second jaw members 12 and 14 for changing the distance between the first and second jaw members 12 and 14. The first jaw member 12 includes the cutting portion of the transcatheter device 10, and thus includes a cutting element 18. The second jaw member 14 serves as a positioning member of the transcatheter device 10.

The device 10 may be coupled to, or part of, a catheter 11 for delivery over a guidewire 13, as is well known in the art.

FIG. 1 illustrates transcatheter device 10 in a stowed (contracted) orientation and being deployed over guidewire 13 to the surgical site. A distal end 19 of transcatheter device 10, which in the illustrated embodiment is the distal end of second jaw member 14, may be tapered and blunt for easy entry and preventing harm to tissue.

Figure 2:
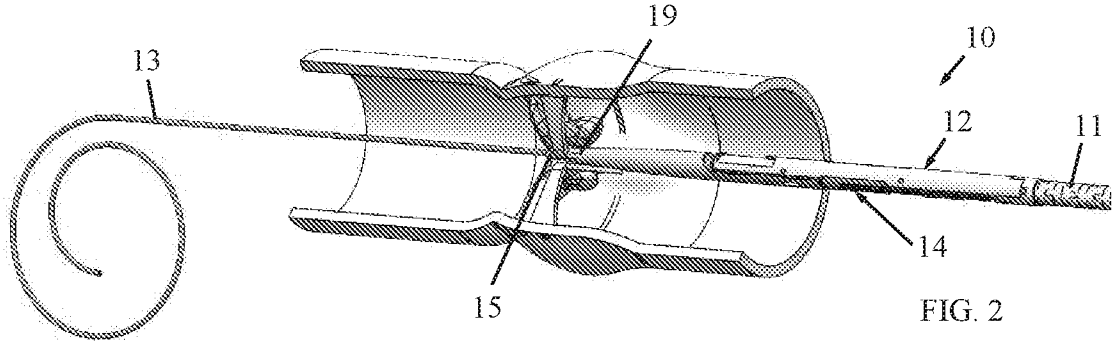
FIG. 2 is a simplified pictorial illustration of the distal end of the transcatheter device touching valve tissue at the surgical site.

FIG. 2 illustrates the distal end 19 of the transcatheter device touching valve tissue 15 at the surgical site.

Figure 3:
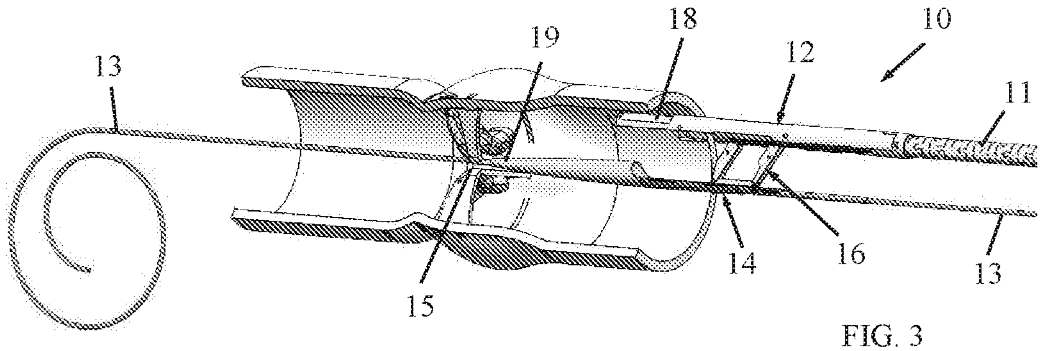
FIG. 3 is a simplified pictorial illustration of a first jaw member (which includes the cutting portion of the transcatheter device) being deployed radially outwards from a second jaw member (which serves as the positioning member of the transcatheter device and/or an anvil or scoring member)

FIG. 3 illustrates first jaw member 12 being deployed radially outwards from second jaw member 14. Second jaw member 14 serves as the positioning member of the transcatheter device 10 by assuring the device 10 is aligned properly with the valve 15, such as being centered with respect to the valve.

Figure 4:
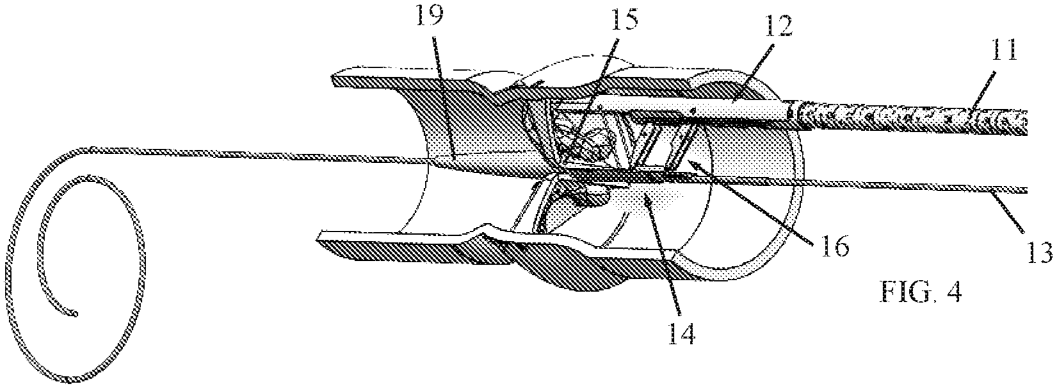
FIG. 4 is a simplified pictorial illustration of the first and second jaw members being advanced distally to the valve tissue.

FIG. 4 illustrates first and second jaw members 12 and 14 being advanced distally to the valve tissue 15.

Figure 5:
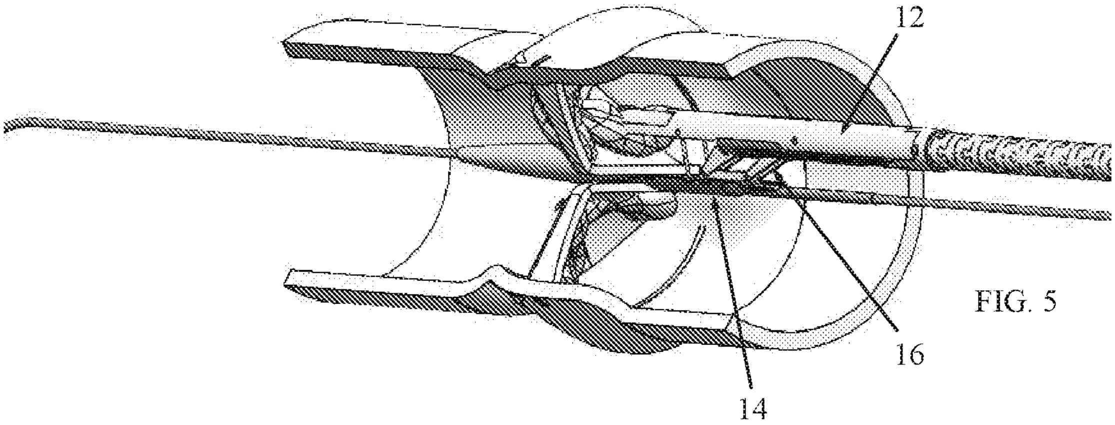
FIG. 5 is a simplified pictorial illustration of reducing the distance between the first and second jaw members.
Figure 6:
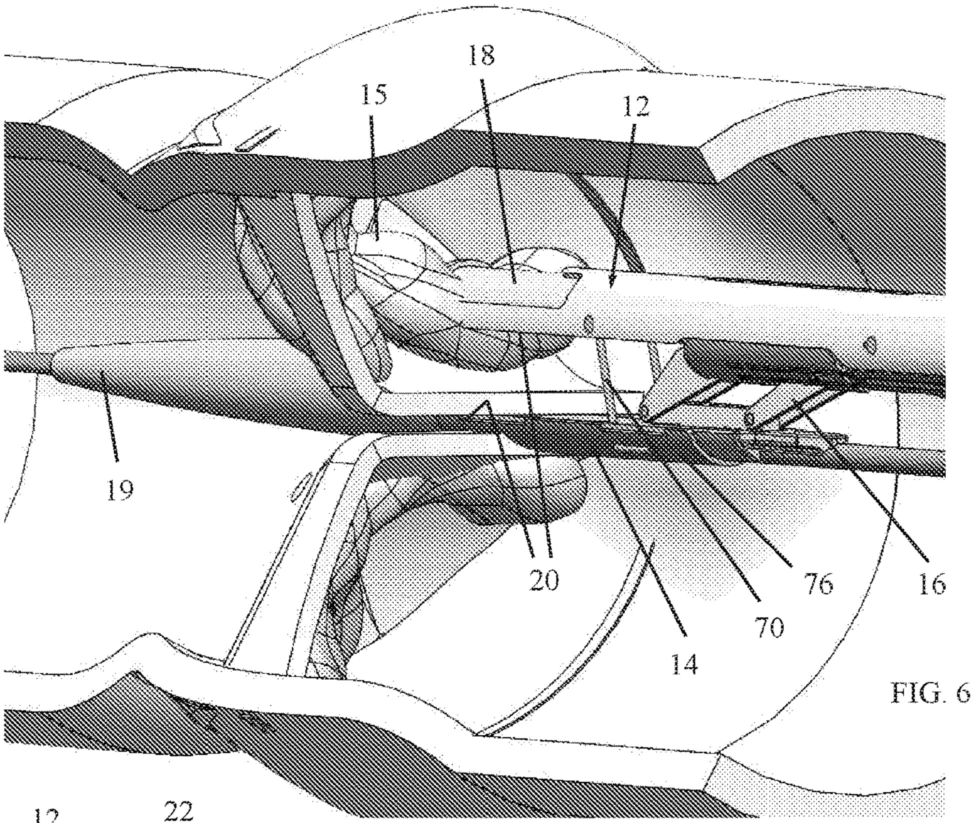
FIG. 6 is an enlarged view of FIG. 5.

FIGS. 5 and 6 illustrate using the linkage mechanism 16 to reduce the distance between the first and second jaw members 12 and 14.

Figure 6A:
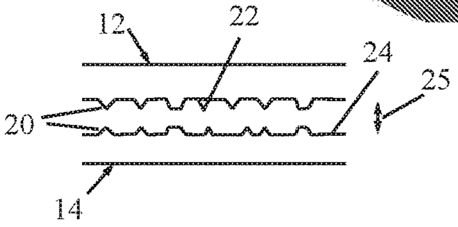
FIG. 6A illustrates scoring structure on either or both of the first and second jaw members.

Reference is now made to FIG. 6A. The first and second jaw members 12 and 14 also have the capability of scoring calcifications (or scoring tissue or any other anatomical structure), and as such, one of the first and second jaw members 12 and 14 may include scoring structure 20 while the other one of the first and second jaw members 12 and 14 serves as an anvil against which the tissue or other anatomical structure is supported to provide a counterforce to the scoring force. Alternatively, both of the first and second jaw members 12 and 14 may include scoring structure 20, so that the anvil also has scoring structure.

The scoring structure 20 is located on either one or both of surfaces 22 and 24 of the first and second jaw members 12 and 14, respectively, which face each other. The direction of the scoring force is along an imaginary axis, referred to as the jaw closing axis 25, which extends between the surfaces 22 and 24.

The scoring structure 20 may include sharp or non-sharp protrusions or any combination thereof, as shown. As seen in FIG. 6A, some of the scoring structure may face each other on both jaw members or only one of the jaw members may have the scoring structure while the opposite jaw member is smooth opposite that scoring structure.

Figure 7:
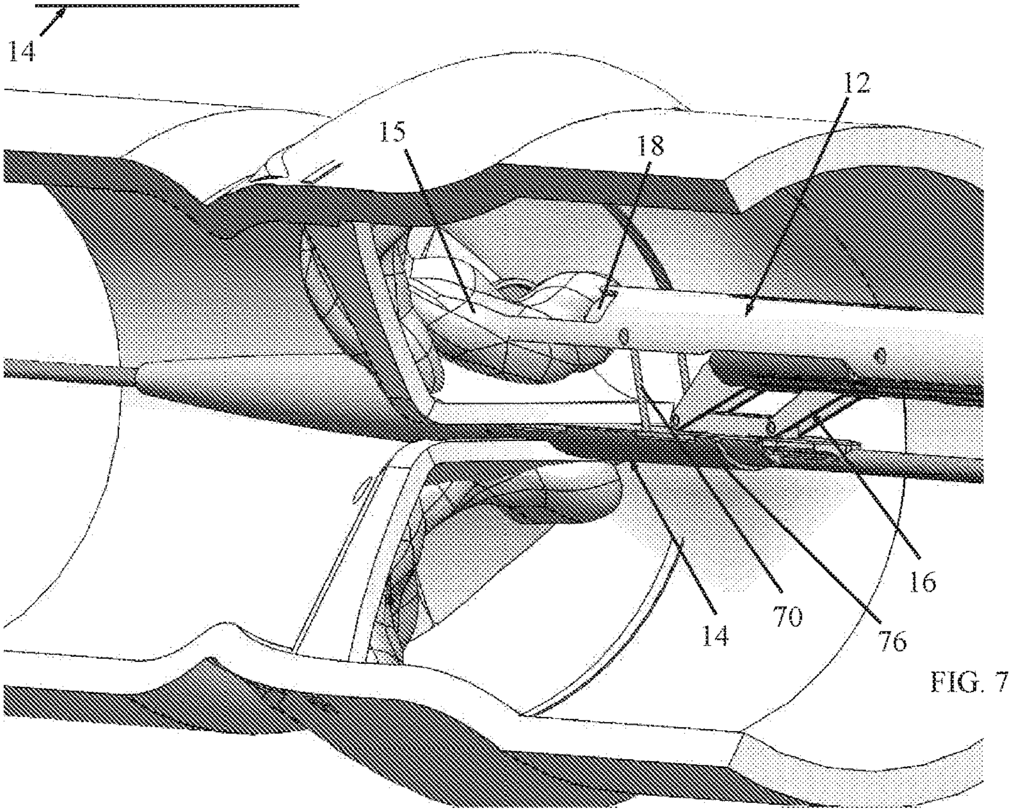
FIG. 7 is a simplified pictorial illustration of a cutting element of the first jaw member moved proximally away from valve tissue prior to slicing the valve tissue.
Figure 8:
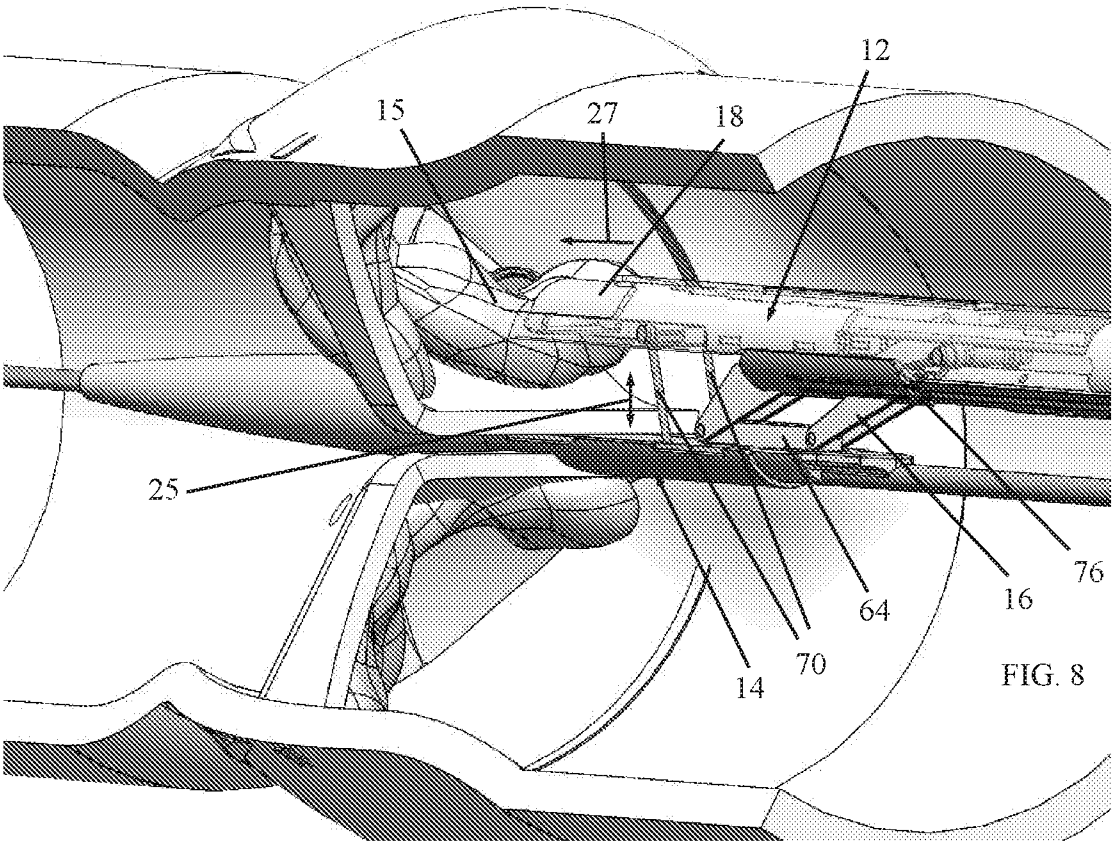
FIG. 8 is a simplified pictorial illustration of the cutting element of the first jaw member moved distally to slice the valve tissue.

Reference is now made to FIG. 7. The cutting element 18 of the first jaw member 12 has been moved proximally away from valve tissue 15 prior to slicing the valve tissue 15. In FIG. 8, the cutting element 18 of first jaw member 12 has been moved distally to slice the valve tissue 15. The slicing (also referred to as cutting) action of cutting element 18 is in a slicing (also referred to as cutting) direction 27 transverse to the jaw closing axis 25. The slicing direction may be along the distal-proximal axis of the device and may be, but is not necessarily, perpendicular to the jaw closing axis 25.

Figure 9:
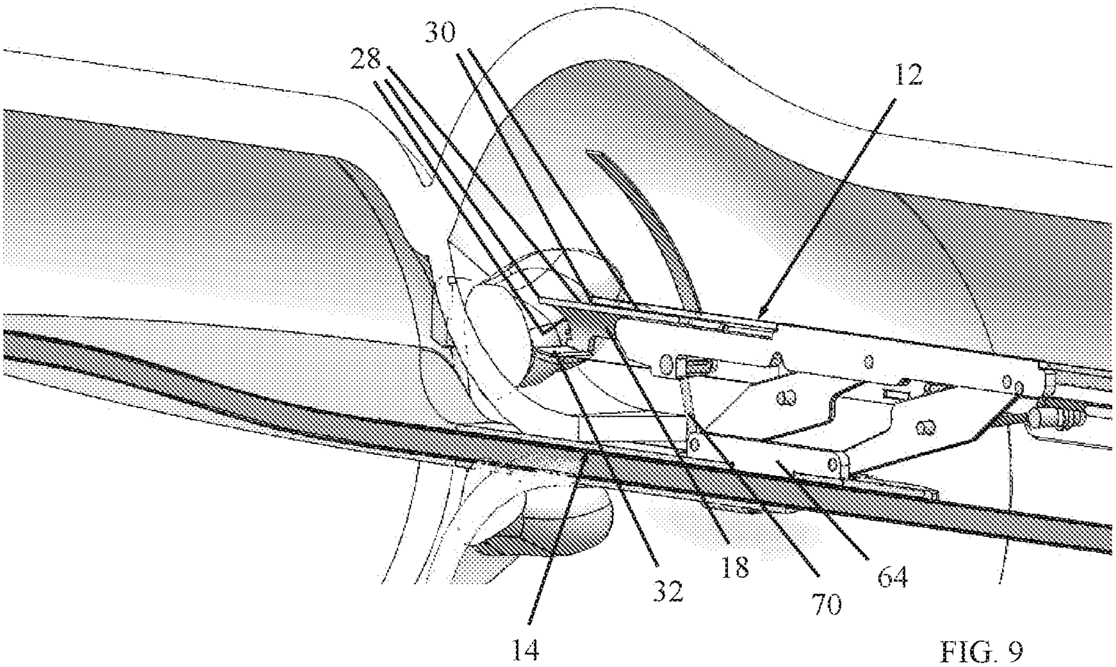
FIG. 9 is a cutaway view of FIG. 8.
Figure 10:
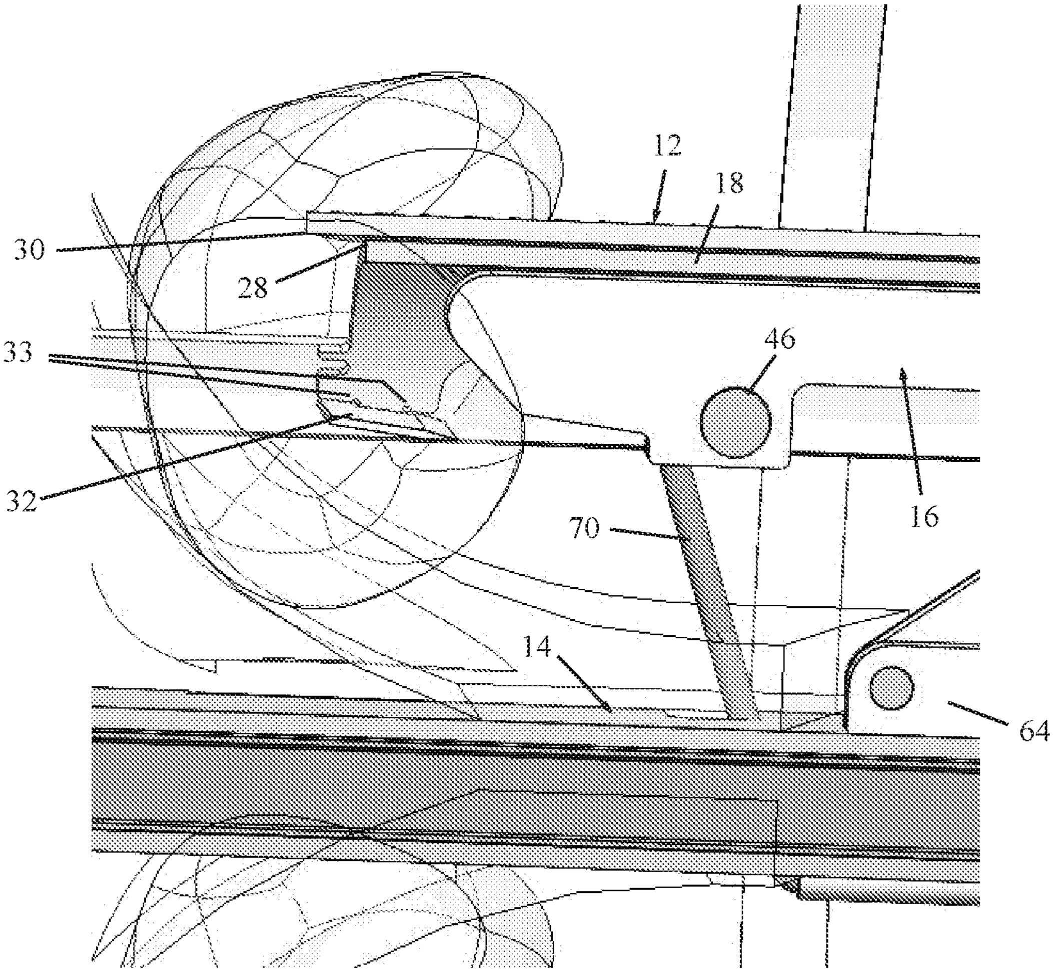
FIG. 10 is an enlarged view of FIG. 9.

FIGS. 9 and 10 illustrate an enlarged view of the cutting element 18. The cutting element 18 may have a sharp edge 28 which alone may be sufficient to cut tissue, but which may be augmented by sliding past a sharp edge 30 of first jaw member 12, which creates a slicing or scissoring effect. The sharp edge 28 of cutting element 18 may be at the distal end of cutting element 18 and/or along its longitudinal length. Likewise, the sharp edge 30 of first jaw member 12 may be at its distal end and/or along its longitudinal length. In the illustrated embodiment, cutting element 18 moves in translation. Alternatively or additionally, the cutting element 18 may be a rotational or oscillating cutting element.

In the illustrated embodiment, cutting element 18 is shaped as a tube with a longitudinal cutout portion. In such a configuration, the inner peripheral portion 33 (FIG. 10) of the distal end of cutting element 18 may be coupled to a cross piece 32, which may help keep the cut tube rigid for easier assembly into first jaw member 12. Alternatively, cutting element 18 may have other shapes, such as but not limited to, a straight knife edge.

Reference is now made to FIGS. 11-25, which illustrate components of the transcatheter device and their assembly with each other.

Figure 11:
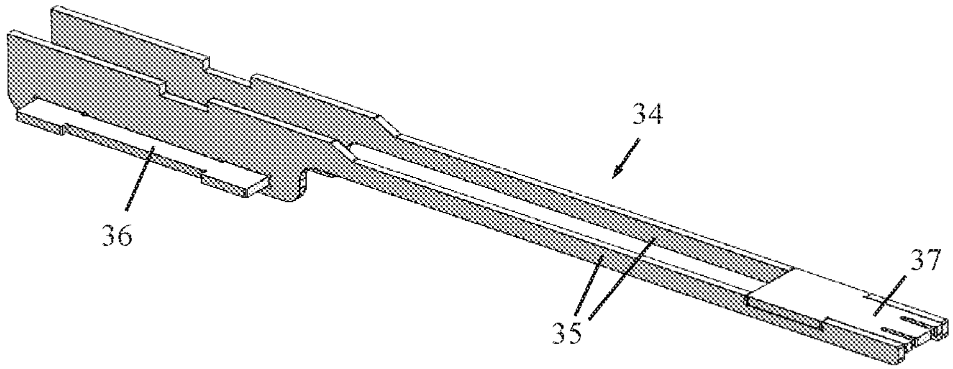

FIG. 11 illustrates a cutter mover 34 which will be coupled to the cutting element 18 (not shown here) at a distal end thereof. In the non-limiting illustrated embodiment, the cutter mover 34 has an elongate shaft 35 (e.g., a pair of elongate bars) with one or more distal fastening members 36 and a proximal interface member 37. The proximal interface member 37 may be coupled to an actuator (not shown) for moving the cutter mover 34 distally and proximally (or alternatively or additionally, in rotation or oscillation, and not just linear motion).

Figure 12:
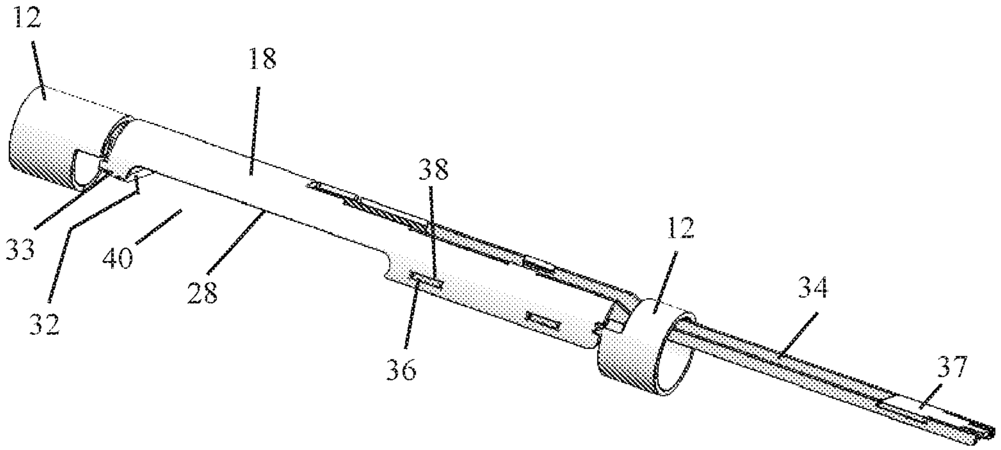
Figure 13:
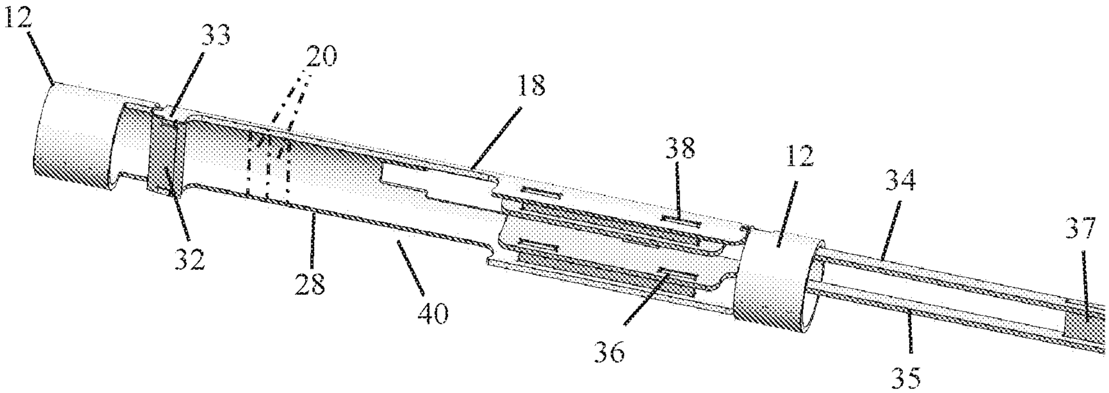

FIGS. 12 and 13 illustrate the cutter mover 34 coupled to the cutting element 18. The one or more distal fastening members 36 may be received in one or more slots 38 formed in cutter element 18 and joined thereat, such as by welding, crimping, swaging, bonding, etc. The cutter element 18 may be formed with an open window 40 on which the surface 22 is located. The sharp edge 28 of cutter element 18 is seen clearly in FIGS. 12 and 13. Part of the scoring structure 20 is shown in broken lines.

Figure 14:
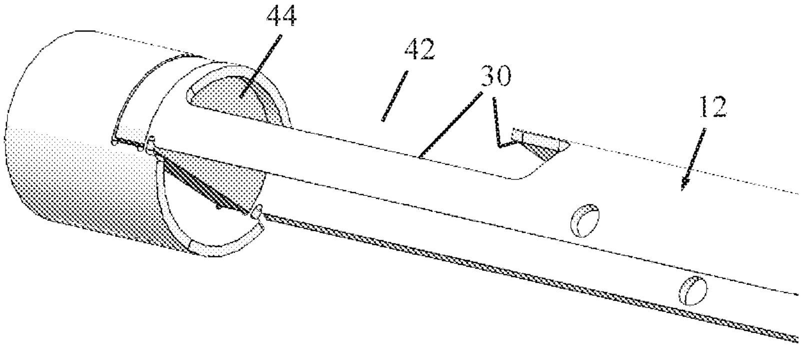
Figure 15:
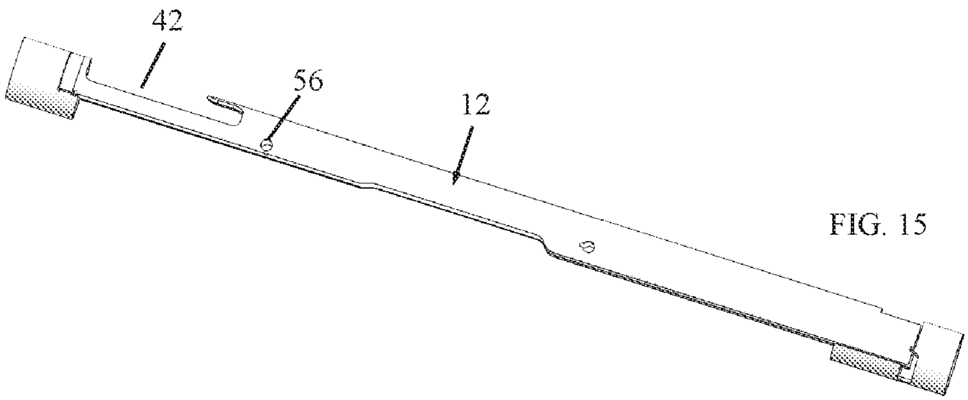

In FIGS. 14 and 15, it is seen that a distal end of the first jaw member 12 may be formed with a cutout window 42, which defines the sharp edge 30 (FIG. 14) of first jaw member 12. The distal end of the first jaw member 12 may include a distal stop 44 (FIG. 14) to limit the travel of the cutting element.

Figure 16:
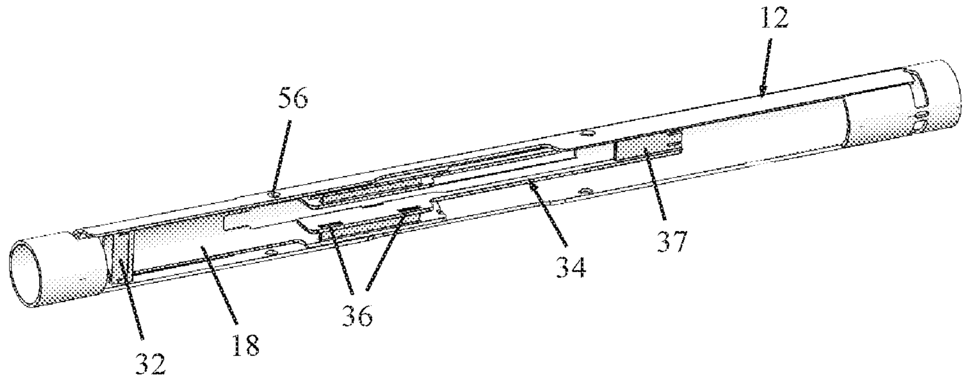

FIG. 16 illustrates the assembly of the cutter mover 34 and the cutting element 18 assembled in the first jaw member 12.

Figure 17:
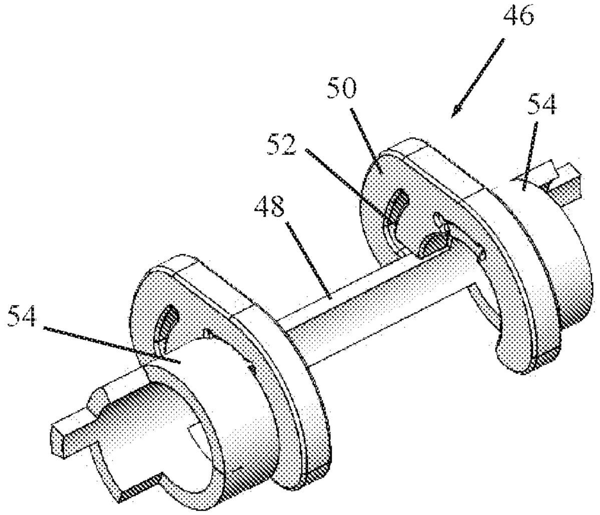

Reference is now made to FIG. 17, which illustrates a pivot member 46 which will be coupled to the first jaw member and to part of the linkage mechanism. The pivot member 46 has an axle 48 on which may be mounted two spaced-apart discs 50, each of which may be formed with an arcuate groove 52. A hub 54 is positioned next to and outwards from each disc 50.

Figure 18:
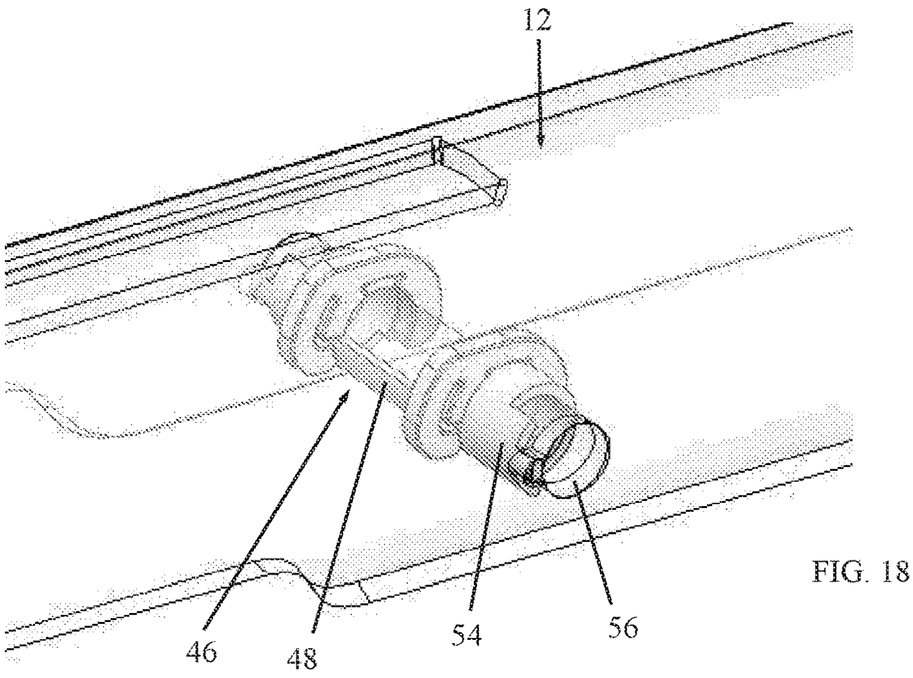

FIG. 18 illustrates the pivot member 46 coupled to the first jaw member 12. The hubs 54 are journaled in bearing holes 56 (which are also seen in FIGS. 15 and 16) formed in first jaw member 12.

Figure 19:
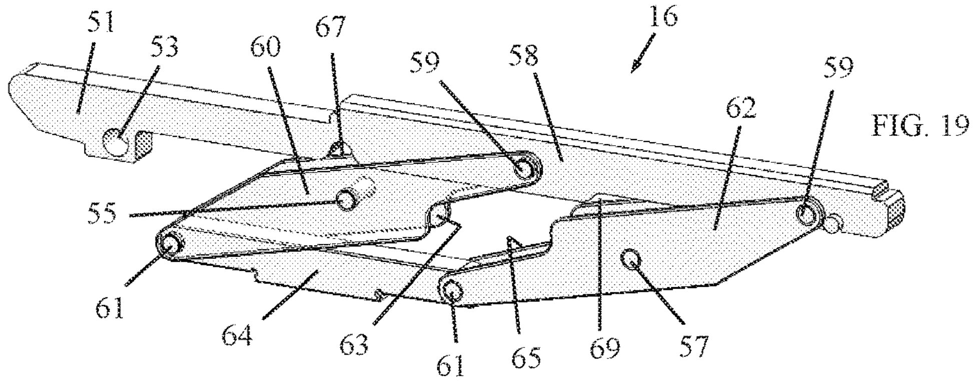

FIG. 19 illustrates the linkage mechanism 16, which will be coupled to the first and second jaw members for changing the distance between the first and second jaw members. In the illustrated non-limiting embodiment, linkage mechanism 16 is a foldable hinged parallelogram mechanism and includes a first bar 58, second bar 60, third bar 62, and fourth bar 64. Throughout their motion, first bar 58 remains parallel with fourth bar 64, and second bar 60 remains parallel with third bar 62. Second bar 60 and third bar 62 are pivoted to first bar 58 at pivots 59, and to fourth bar 64 at pivots 61. Second bar 60 and third bar 62 may be formed with recesses 63 and 65, respectively, so that second bar 60 and third bar 62 nest with each other in the fully folded position.

Second bar 60 and third bar 62 may be constructed as a pair of spaced-apart bars, so that in the fully folded position the first bar 58 and the fourth bar 64 sit in the gap between the spaced-apart bars. First bar 58 may be formed with crevices 67 and 69 to receive therein pins 55 and 57 of second bar 60 and third bar 62, respectively, in the fully folded position.

First bar 58 has a portion 51 that extends beyond the end of second bar 60 and fourth bar 64 in the fully nested position. The portion 51 is formed with an aperture 53.

Figure 20:
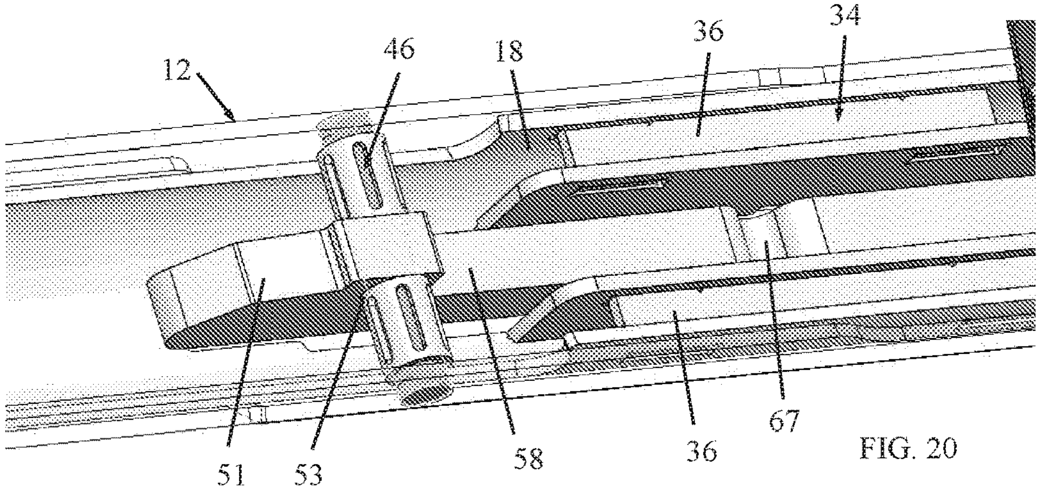

FIG. 20 illustrates the linkage mechanism 16 pivotally coupled to the first jaw member 12 by means of the pivot member 46 that fits through aperture 53 of first bar 58.

Figure 21:
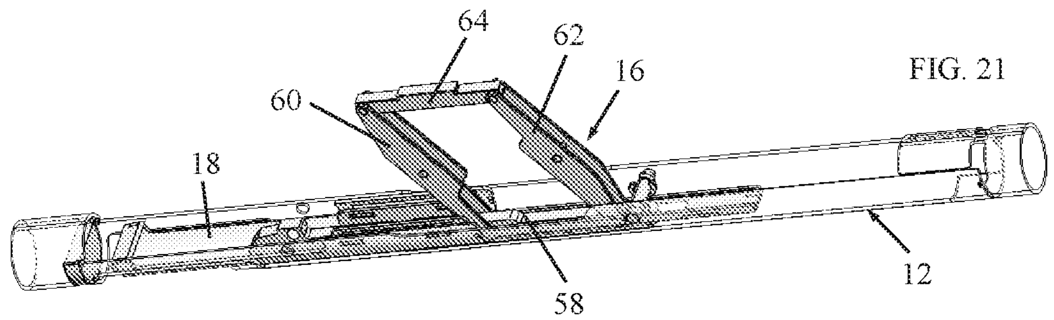
Figure 22:
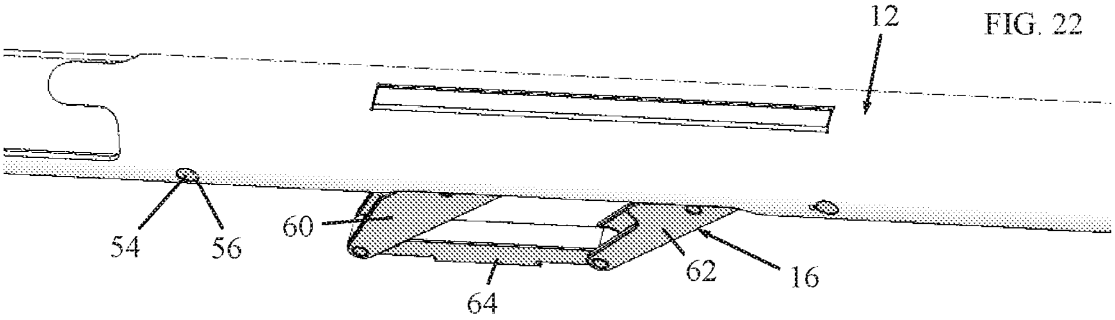

FIGS. 21 and 22 illustrate the linkage mechanism 16 deployed outwards from the first jaw member 12.

Reference is now made again to FIGS. 8, 9 and 10. One or more wires 70 (wire encompassing and slender, wrappable element, such as a wire, cord, and the like) are wrapped around pivot member 46. The distal end of the wire or wires 70 is coupled to second jaw member 14 and the proximal end is coupled to an actuator (not shown) for pulling the wire or wires 70. It is noted that fourth bar 64 is coupled to second jaw member 14. Movement of the wire or wires 70 in the proximal direction causes the bars of the linkage mechanism 16 to move to the fully nested position. Thus, movement of the wire or wires 70 in the proximal direction reduces the distance between the first and second jaw members 12 and 14. This proximal movement of wire or wires 70 thus acts like closing the jaws of a mammal: the wire or wires 70 act like the tendons of the muscles that close the jaw.

Radial outward deployment of the first and second jaw members 12 and 14 may be simply by means of gravity: the second jaw member 14 moves away from the first jaw member 12 by means of the self-weight of the second jaw member 14, if no counterforce is applied by the wire or wires 70. Alternatively, an actuator may be used to move the bars to deploy them outwards with no need to rely on the weight of second jaw member 14.

Figure 23:
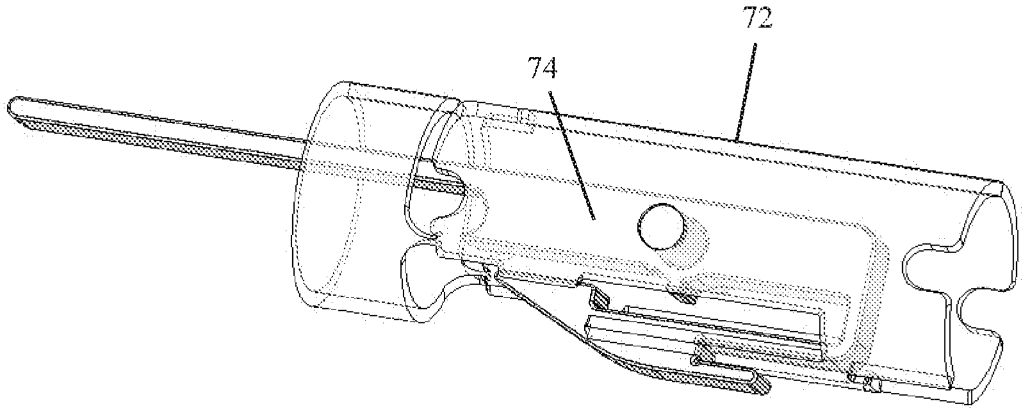
Figure 24:
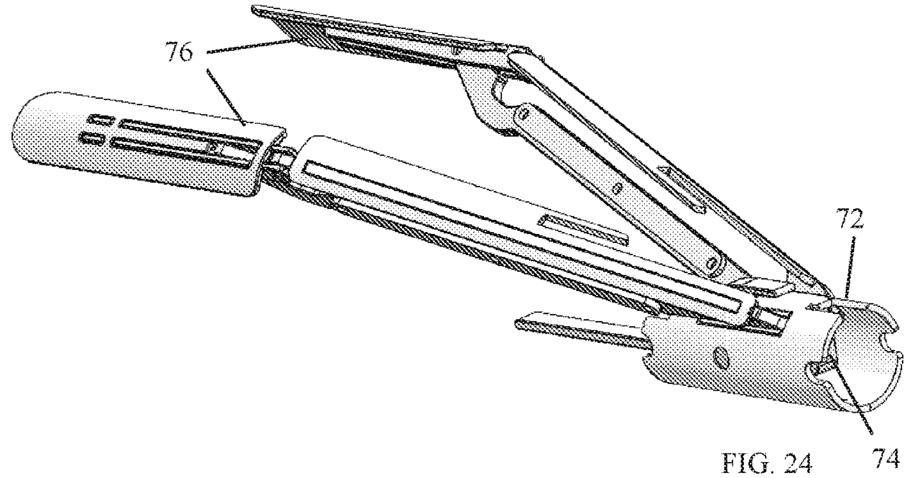

Reference is now made to FIG. 23, which illustrates an actuator interface member 72. The actuator interface member 72 may include a pivotal connector member 74. As seen in FIG. 24, one or more stabilizing arms 76 may be coupled to actuator interface member 72, such as at pivotal connector member 74.

Figure 25:
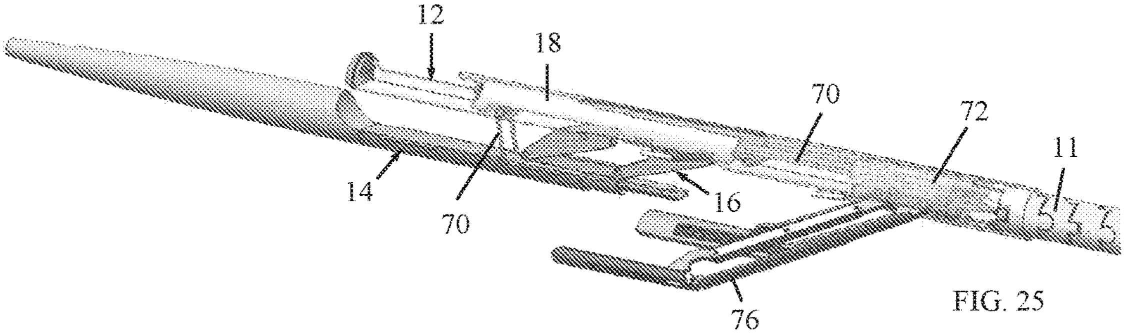

FIG. 25 illustrates the one or more stabilizing arms 76 and the actuator interface member 72 coupled to the first jaw member 12 of the transcatheter device. Movement of the pivotal connector member 74 may deploy the stabilizing arms 76 to the radially outward position shown in FIG. 25, or to the contracted (radially inward) position shown in FIGS. 6, 7 and 8.

Figure 26:
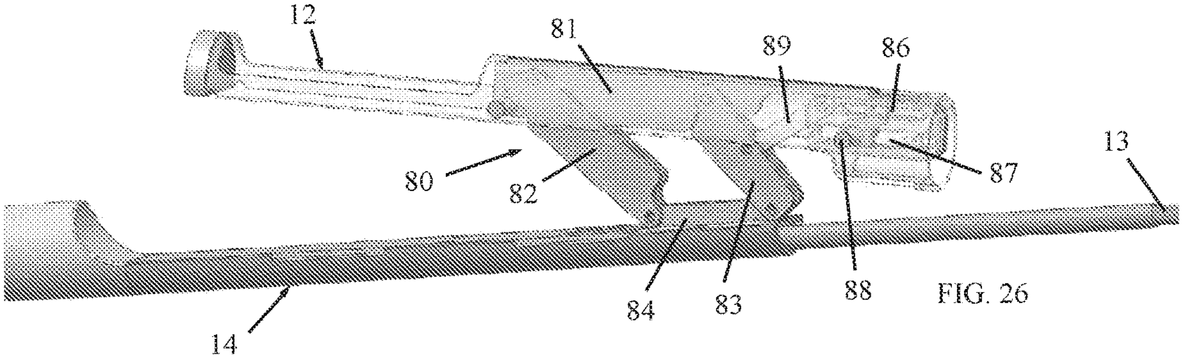
FIG. 26 illustrates another linkage mechanism coupled to the first and second jaw members for changing the distance between the first and second jaw members.

Reference is now made to FIG. 26, which illustrates another linkage mechanism 80 coupled to the first and second jaw members 12 and 14 for changing the distance between the first and second jaw members 14. The linkage mechanism 80 is similar to linkage mechanism 16 in that it is a foldable hinged quadrilateral mechanism (which may be, but not necessarily, kite-shaped), and includes a first bar 81 (coupled to first jaw member 12), second bar 82, third bar 83, and fourth bar 84 (coupled to second jaw member 14). The linkage mechanism 80 is different from linkage mechanism 16 in that it is actuated by an actuator 86, which may slide or otherwise move linearly, such as by a groove 87 which slides relative to a pin 88. The actuator 86 may be pivotally coupled to third bar 83 by a link 89.

What is claimed is:

1. A transcatheter device comprising:

a first jaw member, a second jaw member and a linkage mechanism coupled to said first and second jaw members for changing a distance between said first and second jaw members;

at least one of said first and second jaw members comprising scoring structure capable of scoring calcifications or tissue or any other anatomical structure, wherein a direction of a scoring force applied by said scoring structure is along a jaw closing axis that extends between surfaces of said first and second jaw members, respectively, which face each other; and wherein said first jaw member comprises a cutting element arranged to cut in a cutting direction transverse to said jaw closing axis.

2. The transcatheter device according to claim 1, wherein said linkage mechanism comprises one or more wires wrapped around a pivot member which is coupled to said first jaw member, a distal end of said one or more wires being coupled to said second jaw member, and wherein movement of a proximal end of said one or more wires in a proximal direction reduces a distance between said first and second jaw members.

3. The transcatheter device according to claim 1, wherein said cutting direction is along a distal-proximal axis of the device.

4. The transcatheter device according to claim 1, wherein said cutting direction is perpendicular to said jaw closing axis.

5. The transcatheter device according to claim 1, wherein said scoring structure comprises sharp or non-sharp protrusions or any combination thereof.

6. The transcatheter device according to claim 1, wherein said cutting element comprises a sharp edge movable past a sharp edge of said first jaw member.

7. The transcatheter device according to claim 1, wherein said cutting element is a rotational cutting element.

8. The transcatheter device according to claim 1, wherein said cutting element is an oscillating cutting element.

9. The transcatheter device according to claim 1, wherein said cutting element is shaped as a tube with a longitudinal cutout portion.

10. The transcatheter device according to claim 1, further comprising a cutter mover coupled to said cutting element.

11. The transcatheter device according to claim 1, wherein a distal end of said first jaw member is formed with a cutout window, which defines a sharp edge of said first jaw member.

12. The transcatheter device according to claim 1, wherein a distal end of said first jaw member comprises a distal stop to limit a travel of said cutting element.

* * * * *